United States Patent [19]

Bonaldo

[11] Patent Number: 4,774,964
[45] Date of Patent: Oct. 4, 1988

[54] DISPOSABLE BLOOD COLLECTION DEVICE

[75] Inventor: Jean M. Bonaldo, Upland, Calif.

[73] Assignee: Applied Plastics Technology, Inc., Rancho Cucamonga, Calif.

[21] Appl. No.: 121,959

[22] Filed: Nov. 18, 1987

[51] Int. Cl.$^4$ ............................................. A61B 5/14
[52] U.S. Cl. ....................................... 128/763; 604/52
[58] Field of Search ....................... 128/763, 764, 770; 604/51, 52, 110, 194–198, 181, 228, 263, 272, 411–415

[56] References Cited

U.S. PATENT DOCUMENTS

| | | | |
|---|---|---|---|
| 4,166,450 | 9/1979 | Abramson | 128/764 |
| 4,398,544 | 8/1983 | Nugent et al. | 128/763 |
| 4,507,117 | 3/1985 | Vining et al. | 604/228 |
| 4,592,744 | 6/1986 | Jagger et al. | 128/763 |
| 4,643,199 | 2/1987 | Jennings et al. | 128/763 |
| 4,650,468 | 3/1987 | Jennings | 604/110 |
| 4,675,005 | 6/1987 | DeLuccia | 604/110 |
| 4,692,156 | 9/1987 | Haller | 128/763 |

Primary Examiner—Max Hindenburg
Attorney, Agent, or Firm—Robert R. Thornton

[57] ABSTRACT

A blood collection device wherein a double-ended cannula is retracted within the barrel of the device for storage and disposal. The cannula is mounted on a first disc which is connected to a second axially aligned disc by a pair of string-like flexible members which are operable, when the second disc is moved away from the first disc, to retract the cannula completely within the barrel to a position in which the cannula is permanently locked by stopping the first disc against further retractive movement and the second disc against movement toward the first disc.

20 Claims, 3 Drawing Sheets

DISPOSABLE BLOOD COLLECTION DEVICE

BACKGROUND OF THE INVENTION

1. Field of the Invention

This invention relates to a disposable blood collection device employing a needle which is retracted within a barrel for shipment prior to use, extended for use, and retracted to a permanently locked position within the barrel to protect against accidental needle sticks after the needle has been used. More particularly, it relates to an improved locking system to hold the needle within the barrel during shipping, securely in the locked position.

2. Background Discussion

Medical devices using needles which are retained in a retracted position after the needle is used to guard against accidental sticks are well known. Such devices are shown, for example, in U.S. Pat. No. 4,650,468; 4,675,005; 4,692,156; and 4,507,117. Devices shown in the aforementioned patents are generally of the hypodermic syringe type, that is, a single needle point normally fixed to the end of a barrel and covered by a protective guard is utilized to inject fluids into or extract fluids from the human body. The needle point is retracted into the syringe barrel and retained therein by various means after use.

A somewhat different type of device has come into use with respect to the collection of blood samples. The device includes a double-ended cannula or needle, again is fixed to one end of the barrel and covered by a protective guard prior to use. The guard is removed and the end of the needle so uncovered is inserted into the patient's vein. A sterile evacuated container is applied to the other end within the barrel so that the pressure differential resulting thereby causes blood to be drawn from the vein into the evacuated container. When the container is filled, it is removed from the needle, thereby providing a sealed blood sample in the container. Examples of this type of device are shown in FIGS. 4–6 of U.S. Pat. No. 4,592,744 and in FIGS. 1–3 of U.S. Pat. No. 4,643,199. In each of these devices, a double-ended cannula is normally fixed to the end of the barrel so that one end extends from the barrel and is covered by a protective guard prior to use. After use, the double ended cannula is retracted within the barrel so as to be disposable without the danger of sticking personnel thereafter handling it. However, both of these devices require the user to use both hands in order to retract the needle after use, and thus are relative complicated and time consuming in use. In addition, having the patient-inserted end of the cannula normally fixed to the end of the barrel takes up additional shipping space and requires removal of the guard prior to use.

SUMMARY OF THE INVENTION

A blood collection device has a double-ended cannula disposed in a barrel, open at one end to permit the insertion of an evacuated sample collection container therein onto one end of the double-ended cannula, and an aperture at the other barrel end to permit the extension and retraction therethrough of the other end of the double-ended cannula, with a first disc disposed within the barrel and to which the double-ended cannula is fixed so as to extend to each side thereof and be axially aligned within the barrel in a shipping position in which the cannula is completely contained within the barrel prior to use, and having a second disc disposed within the barrel between the first disc and the barrel open end, said second disc having an aperture axially formed therein so as to permit one end of the cannula to pass therethrough, the first disc and the second disc being connected to together by connectors within the barrel to permit preselected relative movement therebetween so that when the second disc is moved toward the barrel closed end, the first disc is moved against the barrel closed end, in which position the other end of the cannula extends out of the barrel aperture, and when said second disc is thereafter moved to a disposal position adjacent to barrel open end, the first disc is withdrawn by said connectors from the barrel closed end in a spaced-apart relationship from the second disc to a position in which both ends of the cannula are disposed within the barrel, with locking means for locking the first disc and second disc within the barrel in said spaced-apart relationship and manual operating means operable for initiating the movement of said discs to said spaced-apart relationship in conjunction with said connectors.

BRIEF DESCRIPTION OF THE DRAWING

The blood collection device of this invention is illustrated in the drawing, with like numerals indicating like parts, and in which.

DETAILED DESCRIPTION OF THE INVENTION

Figure 1:
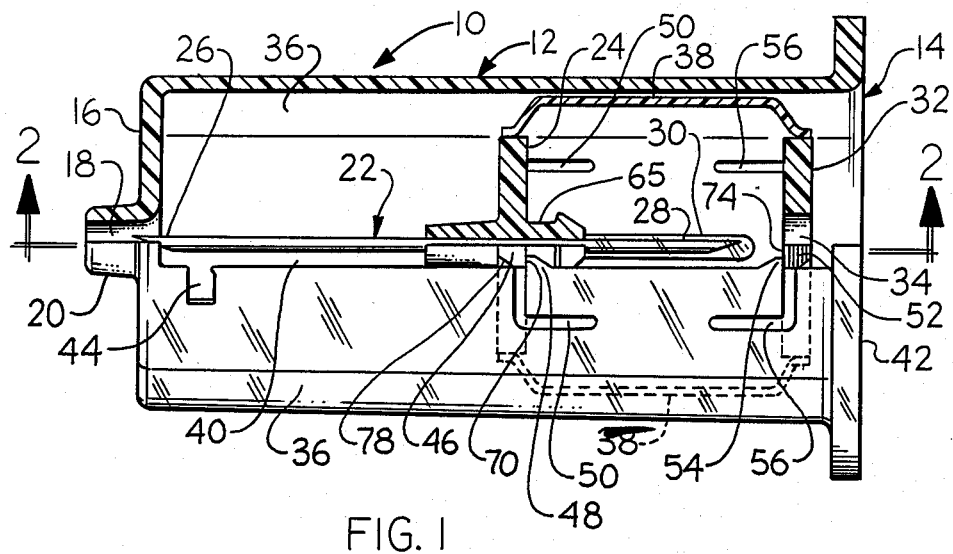
FIG. 1 is a side elevational view, partially broken away, of the blood collection device of this invention in its disposable disposition.
Figure 2:
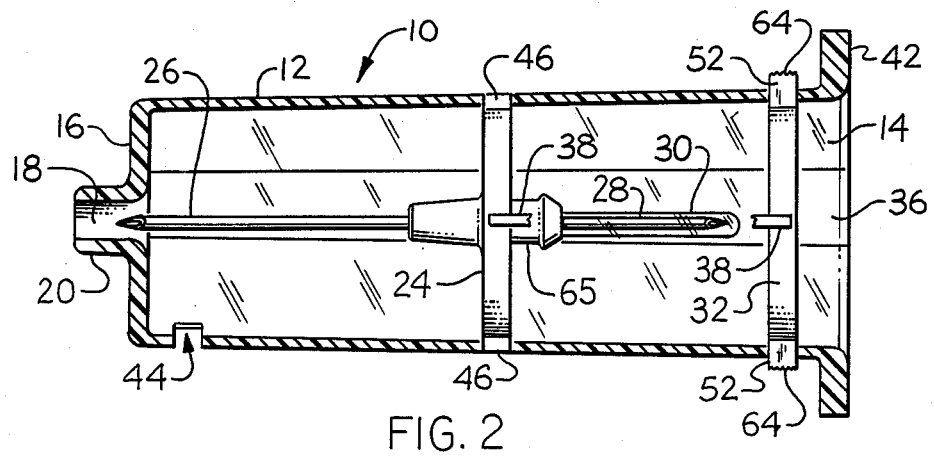
FIG. 2 is a plan view, taken along line 2—2 of FIG. 1.

Referring now to FIG. 1, there is shown a blood collection device 10 which has a barrel 12 with an open end 14 and a generally closed end 16, through which an aperture 18 is formed within a boss 20. A double ended cannula 22 is mounted within the barrel 12 by means of a first disc 24 through which the cannula 22 extends so as to be axially aligned with the barrel. The disc 24 is mounted on the cannula 22 so that a first blood collecting needle 26 may be extended through the boss aperture 18 by movement of the first disc 24 toward the closed end 16 in the disposition shown in FIG. 2 and may be retracted to the disposition shown in FIG. 1 by movement of the first disc 24 away from the closed end 16.

The double ended cannula 22 has a sample transfer needle 28 which is enclosed within a latex or similar sheath 30 and is used in conventional fashion to transfer the blood from the patient through the collecting needle 26 into an evacuated sample collection container of conventional configuration, which is inserted onto the blood collecting needle 26. Such sample collection containers are well known and are sold, for example, under the trademark, manufactured by Becton-Dickinson Company, Rutherford, New Jersey.

Figure 5:
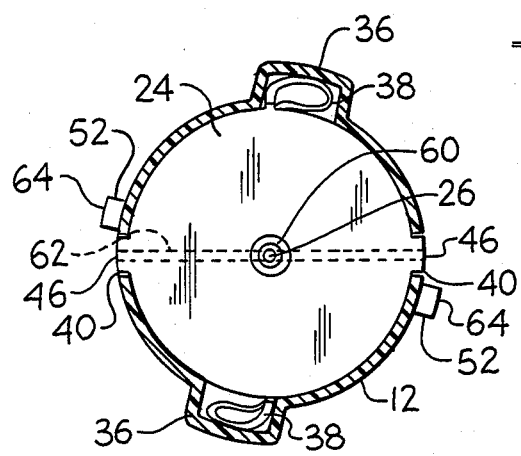
FIG. 5 is a cross-sectional view taken along line 5—5 of FIG. 4.

A second disc 32 is disposed within the barrel 12 so as to be located between the first disc 24 and the barrel open end 14. The second disc 32 has an aperture 34 axially formed therein so as to permit the passage therethrough of the sample transfer needle 28 and sheath 30. The barrel 12 is not of completely circular cross-section, but rather has a pair of channels 36 formed on opposite sides thereof, as is more clearly shown in FIG. 5. Disposed within the channels 36 are a pair of string-like flexible connectors 38, which are connected between the first disc 24 and the second disc 32. The barrel 12 has a pair of oppositely disposed longitudinal passages 40 terminating at the barrel open end 14 in a flange 42 which surrounds the open end 14. The longitudinal passages 40 terminate at the closed end 16 in offset openings 44. The first disc 24 has a pair of first disc ears 46 oppositely disposed at the outer periphery thereof so as to extend into the longitudinal passages 40. In disposition of the device 10 shown in FIG. 1, the first disc ears 46 each abut a first lug 48 formed on the barrel 12 adjacent a first pair of laterally aligned L-shaped apertures 50. The second disc 32 has a pair of second disc ears 52 which, in FIG. 1, are disposed just beyond a pair of second disc stop lugs 54 located adjacent a second pair of L-shaped apertures 56. The respective L-shaped apertures 50, 56 on each side of the barrel 12 point toward one another.

Figure 3:
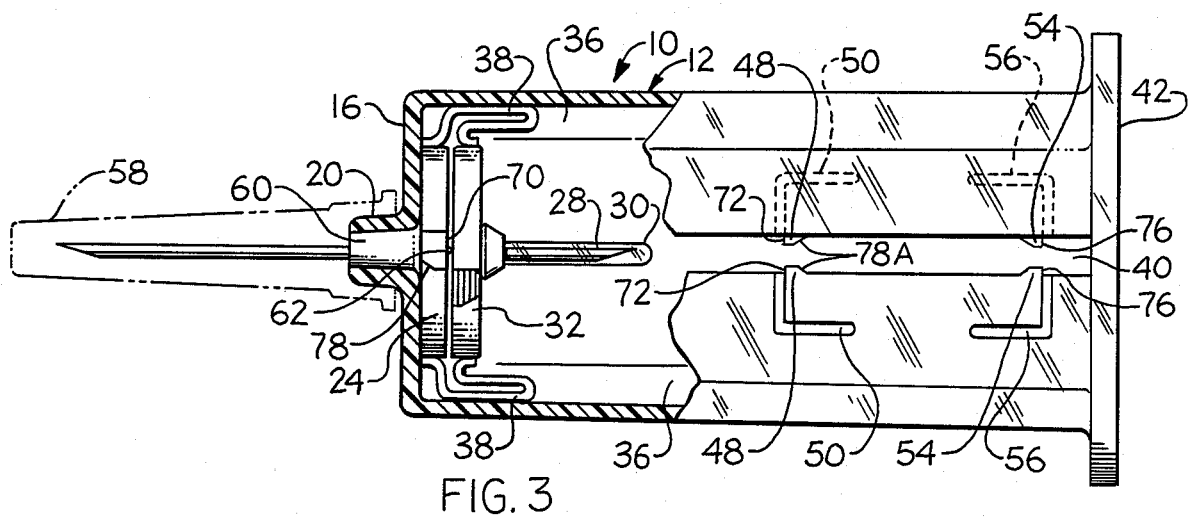
FIG. 3 is a side elevational view, partially broken away, of the improved blood collection device of this invention, in its operating disposition.

Referring now to FIG. 3, there is shown a side elevation, partially broken away, of blood collection device 10 with the cannula 22 in its extended position. A sheath 58, shown in dotted lines, may be utilized to protect the blood collection needle 26 prior to insertion into the patient's vein. In FIG. 3, the first disc 24 has been moved laterally to abut the closed end 16 so that the blood collection needle 26 extends through the aperture 18 formed in the boss 20 so as to be in the operating position. As is shown in FIG. 3, the first disc 24 utilizes a blood collection needle hub 60 which extends outwardly axially from the first disc 24 to seat in the aperture 18 formed in the boss 20 to provide a rigid seat for the blood collection needle 26 to the first disc 24 in the barrel 12.

The second disc 32 is shown in FIG. 3 as having been moved adjacent the first disc 24 so as to be spaced therefrom by a small rib 62 formed on the face of the first disc. The first disc 24 is moved into the position shown in FIG. 3 by movement of the second disc 32 applied manually to the second disc ears 52 at a finger engagement portion 64 thereof (see FIG. 2). The second disc ears 52 are disposed and locked in the offset openings 44 formed in the barrel 12 when the blood collection device 10 is in the configuration shown in FIG. 3, as is more clearly shown in FIG. 4.

Figure 4:
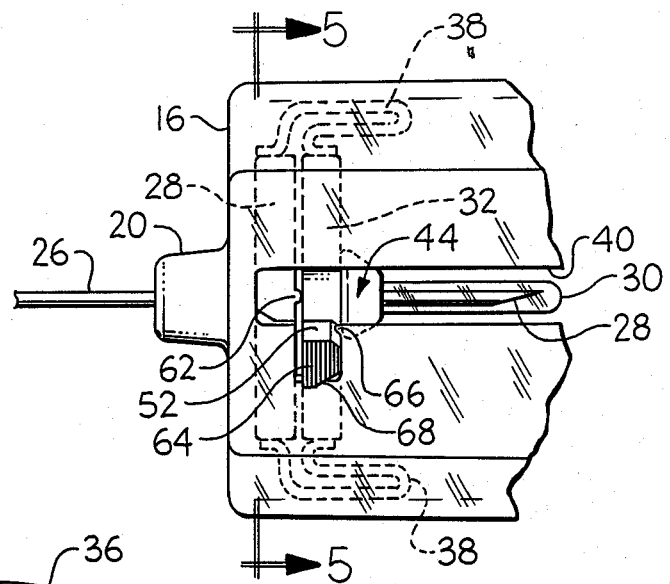
FIG. 4 is a partial side elevational view of the improved blood collection device in its operating disposition.

Referring now to FIG. 4, there is shown a partial side elevation of the blood collection device 10 illustrating the manner in which the blood collecting needle 26 is locked in the extended position. As will be seen in FIG. 4, the first disc 24 abuts the closed end 16 of the barrel 12. The second disc 32 is spaced from the first disc 24 by the rib 62. However, the second disc 32 has been rotated clockwise about a hub 65 formed on the first disc 24 opposite the blood collection needle hub 60 from the position shown in FIG. 1 so as to have the second disc ears 52 disposed in the offset openings 44. The ears 52 are locked in this position by means of small bosses 66 formed on the barrel 12 at the edge of the offset openings 44. When it is desired to retract the blood collection needle 26, the second disc ears 52 are rotated counterclockwise manually so as to override the small bosses 66 and move the second disc ears 52 into the longitudinal passages 40. The second disc 32 is then moved toward the open end 14 of the barrel 12 by manual pressure on the finger engagement portions 64. This longitudinal movement away from the closed end 16 of the barrel 12 causes the flexible string-like connectors 38, which are in a coiled disposition in FIG. 4, to become extended to the general configuration shown in FIGS. 1 and 2, at which time continued movement of the second disc 32 toward the open end 14 causes the connectors 38 to pull the first disc 24 away from the closed end 16, thereby retracting the blood collection cannula 26 into the barrel 12.

Figure 6A:
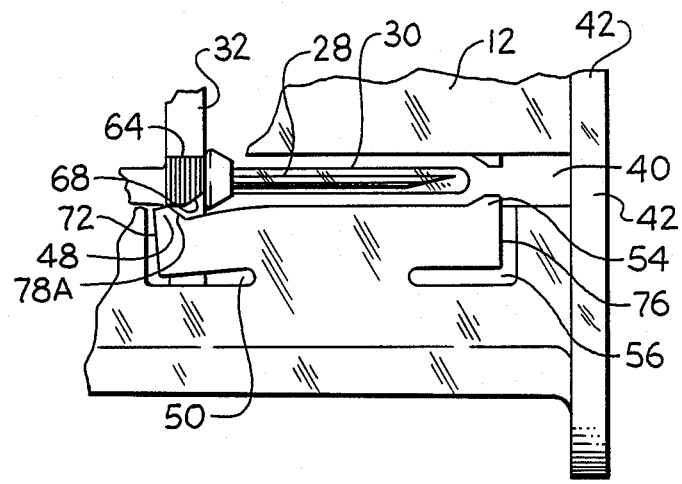
FIG. 6, parts A and B being taken together, is a partial side elevational view showing the details of the locking operation of the device of the present invention.
Figure 6B:
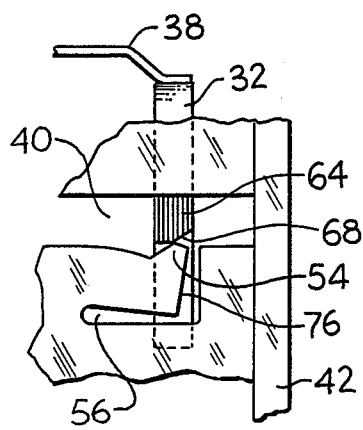

As the second disc 32 reaches the first disc stop lugs 48, the first disc stop lugs 48 contact camming faces 68 formed on the second disc ears 52 so as to taper inwardly toward the open end 14. Further longitudinal movement of the second disc ears 52 then depresses the first disc stop lugs 48 by reason of the L-shaped aperture construction (see FIG. 6A), so that the second disc ears 52 override the first disc stop lugs 48 to permit the second disc 32 to pass beyond the first disc stop lugs 48 and approach the second disc stop lugs 54. When the second disc ears 52 reach the second disc stop lugs 54, the camming surfaces 68 permit the ears 52 to override the second disc stop lugs 54 by depressing the lugs 54 (see FIG. 6B) so as to permit the second disc 32 to pass thereby.

The first and second discs 24, 32 are then in a disposition shown in FIG. 1, in which the first disc ear flat faces 70 abut the first disc ears 46, which are unable to depress the first disc stop lugs 48 by reason of the flat faces 70 on the ears 52 abutting flat faces 72 on the first disc stop lugs 48. Similarly, the second disc ears 52 have flat faces 74 which abut flat faces 76 on the second disc stop lugs 54, so as to prevent the depressing of the second disc stop lugs 54 otherwise necessary to permit reverse movement of the second disc 32 toward the first disc 24. The first and second discs are thereby locked in the disposition shown in FIG. 1, in which the blood collection needle 26 is retracted within the barrel 12 and the sample transfer needle 28 is contained within the barrel 12 short of the open end 14 thereof. The blood collection device, having been used, is therefore in condition for disposal, with both needle points being contained within the barrel 12 so that the personnel involved in disposition are protected from being stuck by either end of the double ended cannula 22.

In the present invention, it is desirable, but not essential, to secure the cannula blood collection needle 26 within the barrel 12 during shipping, storage, and similar handling prior to actual use, in order to avoid possible contamination of the needle or accidental sticks. To this end, the blood collection device 10 may be assembled so that first disc 24 is disposed between the first disc stop lug 48 and the second disc stop lug 54, so as to be in proximity to the second disc 32 which is also disposed therebetween. When so disposed, the first disc stop lug will be stopped by the first disc ear 46 so as to prevent the first disc 24 from passing thereby toward the barrel aperture 18, thus preventing the blood collection needle 26 from inadvertently being extended through the barrel aperture 18. In order to permit the first disc 24 to be intentionally moved past the first disc stop lug 48, the first disc ear 46 has a camming surface 78 formed thereon, and the first disc stop lug 48 has a complementary camming surface 78A formed thereon. When the first disc 24 in being urged toward the barrel aperture 18, reaches the first disc stop lug 48, the camming surfaces 78, 78A engage, so as to depress the first disc stop lug 48 to permit the first disc 24 to pass thereby toward the barrel aperture 18.

Figure 7:
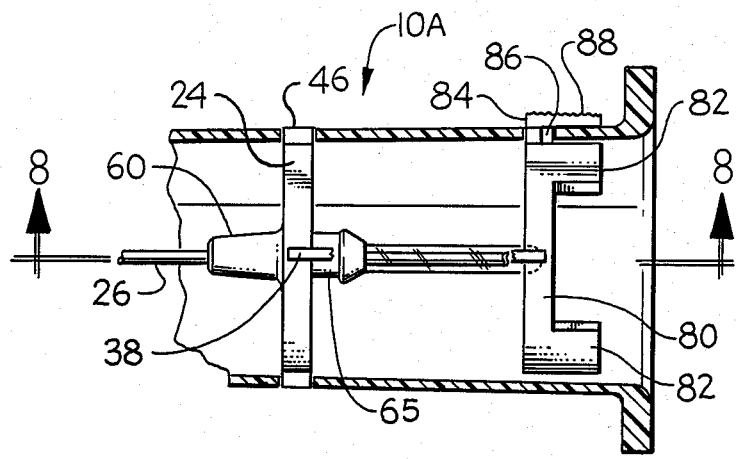
FIG. 7 is a partial side elevational view, in partial cross-section, of an alternate embodiment of the present invention.

Referring now to FIG. 7, there is shown an alternate embodiment of the blood collection device of the present invention, which, instead of using a pair of second disc ears 52, with each having its own finger engagement portion 64, utilizes a single ear and finger engagement portion on the second disc, of somewhat greater dimension, so as to provide for retraction of the second disc by the user's thumb. Longitudinal stabilizing tabs on the second disc provide for disc axial alignment in the barrel. As shown in FIG. 7, a blood collection device 10A has a barrel 12A similar to the barrel 12 of the blood collection device 10 and a first disc 24 with first disc ears 46 which engage first stop lugs 48 in the same manner and of the same construction as those described heretofore with respect to the blood collection device 10. The first disc 24 is, in all respects, identical to the first disc heretofore described. The blood collection device 10A has a second disc 80 to which flexible connectors 38 are attached which are also attached to the first disc 24 in the same manner as before.

Figure 8:
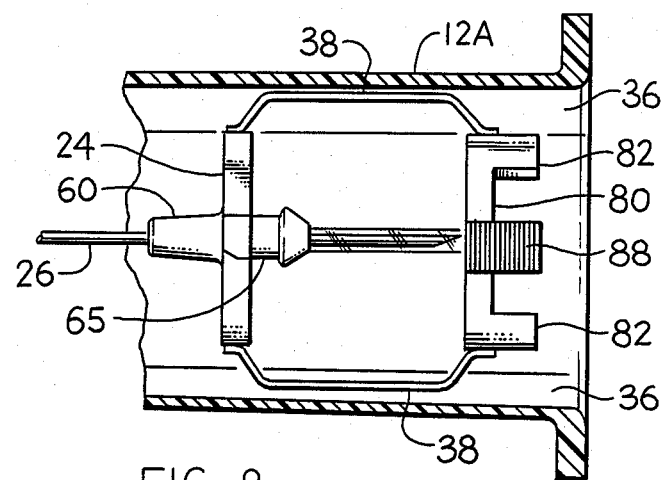
FIG. 8 is a plan view, in partial cross-section, taken along line 8—8 of FIG. 7.

The second disc 80 has four longitudinal stabilizing tabs extending laterally therefrom at the periphery thereof to to provide axial alignment of the second disc 80 in the barrel 12A. The second disc 80 has a single second disc ear 84 which extends into a single longitudinal passage (not shown) on the barrel 12A of the same configuration as the longitudinal passages 40 of the barrel 12, including the L-shaped apertures, disc stop lugs, and offset opening. A camming surface 86 formed on the second disc ear 84 functions in the same manner as the camming surfaces 68 on the second disc ear 52 of the previously described embodiment. The second disc ear 84 has an enlarged finger engagement portion 88, suitable for permitting the use to move the second disc 80 by simply grasping the barrel 12A in one hand and applying the thumb of that hand to the finger engagement portion. In all other respects and operation, the embodiment of FIGS. 7 and 8 is generally identical to that of the embodiment of FIGS. 1 through 6.

In the two embodiments heretofore described, the second disc is utilized to move the first disc toward the barrel aperture by physically contacting the first disc and pushing the first disc toward the barrel aperture. When the first disc 24 contacts the barrel closed end 16, the second disc 32 is rotated so as to rotate the second disc ear 52 into the offset opening 44 so as to lock the blood collecting cannula 26 in the extended or operating disposition. When the blood collecting cannula is to be removed from the patient's vein, the second disc 32 is rotated in the opposite direction to unlock the blood collecting cannula 26 from its operating position. The second disc 32 is then manually moved toward the barrel open end by urging applied by the user to the finger engagement portion 64, 88, as appropriate. The blood collecting cannula is thereby retracted directly from the patient's vein into the barrel 12 without movement of the barrel. This is an important advantage of the present invention, as it precludes any possibility of an inadvertent stick during retraction, and also tends to contain any blood from in the cannula 26 in the barrel closed end 16.

It is, however, possible to utilize various of the aspects of the present invention, particularly with respect to the locking system for the discs, in an embodiment in which the first disc is manually moved directly from the shipping position to the operating position. In such an embodiment, it is necessary to lock the first disc in the needle extended position, which can be accomplished by using an offset opening similar to the opening 44, but positioned so as to receive the first disc ear, rather than the second disc ear. One undersirable aspect of such an embodiment, however, is that, after use, it is either necessary to extract the needle from the patient while in the locked position, in which event the neddle point remains exposed and may result in sticks, or it is necessary to rotate the first disc so as to the unlock the disc to permit retraction while the needle is still inserted in the patient, which is an extremely undersirable practice. Consequently, the preferred embodiment of the invention utilizes the second disc as the element to which the manual urging is applied to accomplish the longitudinal movement of the first disc both toward and away from the barrel aperture.

The connectors 38 may take various forms. In the preferred embodiment, they are string or thread-like plastic. One obvious equivalent configuration is a ribbon. Another is a spring. The terms "thread-like connectors" and "string-like connectors" include such structures. Other types of functionally equivalent structures may be substituted for the thread-like connectors shown in the drawings within the concept and scope of the claims for the present invention to provide for the spaced-apart disposition of the disc in the locked disposal disposition in conjunction with the locking system of the present invention. While in the preferred embodiment, the connectors 38 are stretchable, that is, elastic, particular embodiments of the present invnetion may use connectors which are inelastic to provide the spaced-apart relationship of the discs in the locked disposal dispostion. Similarly, the materials from which the connector are made are not limited to plastics, but plastic materials are presently preferred for ease of fabrication and shelf life.

The invention claimed is:

1. In a blood collection device of the type having a barrel open at one end to permit the insertion of an evacuated sample collection container therein and having an aperture at the other end to permit the extension and retraction therethrough of one end of a double-ended cannula, the combination of:

a first disc disposed within the barrel and through which the double-ended cannula extends so as to be axially aligned within the barrel, said cannula being fixed to said first disc;

a second disc disposed within the barrel between the first disc and the barrel open end, said second disc having an aperture axially formed therein so as to permit one end of the cannula to pass therethrough;

connecting means connected between the first disc and the second disc within the barrel and operable in response to the movement of a preselected one of said discs away from the barrel closed end after the first disc has been moved adjacent thereto so as to extend said one end of the cannula through the barrel aperture to retract said one end of the cannula from the aperture into the barrel so that said preselected one of said discs is in a spaced-apart disposition from the other disc and both ends of the cannula are disposed within the barrel;

locking means for locking the first disc and second disc within the barrel in said spaced-apart disposition; and manual operating means connected to said preselected one of said discs and extending laterally outwardly therefrom and operable in conjunction with said connecting means for the manual movement of said discs to said spaced-apart disposition.

2. The blood collection device of to claim 1, and in which the locking means includes first barrel stop means disposed on the barrel between the barrel closed end and the barrel open end, second barrel stop means disposed on the barrel between the first stop means and the barrel open end, first disc stop means fixed to said first disc, and second disc stop means fixed to said second disc, and in which said first disc stop means is operable in conjunction with said first barrel stop means to prevent the passage of the first disc past the first barrel stop means in the direction of the barrel open end, the second disc stop means is operable in conjunction with the first barrel stop means to permit the passage of the second disc past the first barrel stop means in either the direction of the barrel open end or the direction of the barrel closed end, and the second disc stop means is operable in conjunction with the second barrel stop means to permit passage of the second disc past the second barrel stop means in the direction of the barrel open end and to prevent passage of the second disc past the second barrel stop means in the direction of the barrel closed end.

3. The blood collection device of claim 2, and in which said first and second barrel stop means are each comprised by a generally L-shaped recess formed in the barrel and opening into a longitudinal passage extending substantially the length of the barrel, said L-shaped recesses pointing toward one another, a first lug formed on the barrel at the opening of said recess closest to said barrel closed end and extending into the longitudinal passage so as to be undercut by its respective L-shaped recess, and a second lug formed on the barrel at the opening of said recess closest to said barrel open end and extending into the longitudinal passage so as to be undercut by its respective L-shaped recess.

4. The blood collection device of claim 3, and in which said first disc stop means is comprised by a first disc ear extending radially outwardly from said first disc into said longitudinal passage, and said second disc stop means is comprised by a second disc ear extending radially outwardly from said second disc into said longitudinal passage.

5. The blood collection device of claim 4, and in which the second disc ear has a camming surface formed thereon facing in the direction of the barrel open end and operable to deflect the second lug out of the longitudinal passage to permit passage of the second disc thereby in the direction of the barrel open end, said second ear having a stop surface formed thereon opposite said camming surface and operable when in abutment with the second lug to prevent passage of the second disc thereby in the direction of the barrel closed end.

6. The blood collection device of claim 5, and in which the first disc ear has a stop surface formed thereon facing the barrel open end and operable when in abutment with the first lug to prevent passage of the first disc thereby in the direction of the barrel open end.

7. The blood collection device of claim 6, and in which the barrel longitudinal passage has an offset opening formed so as to open thereinto adjacent the barrel closed end, said offset opening being so disposed that a preselected one of said disc ears can be rotated thereinto when said disc is disposed at the barrel closed end, and locking means formed in said offset opening and operable to engage said disc ear when rotated into said offset opening to normally retain said disc ear in said opening so as to hold said cannula one end in the disposition in which it is extended through the barrel aperture.

8. A blood collection device comprising:

a double-ended cannula;

a barrel closed at one end with an axially disposed aperture formed therein so as to permit the extension and retraction through said barrel aperture of one end of the cannula, said barrel being generally open at the other end to permit the insertion of an evacuated sample collection container onto the other end of said cannula;

a first disc transversely disposed within the barrel and to which the double-ended cannula is fixed so that said one end of the cannula is disposed to one side thereof and said other end of the cannula is disposed to the otherside thereof, said cannula thereby being axially aligned with the barrel, said first disc normally being disposed within said barrel in a shipping position in which both ends of the double-ended cannula are contained within the barrel;

a second disc transversely disposed within the barrel between the first disc and the barrel open end, said second disc having an aperture axially formed therein so as to permit said other end of the cannula to pass therethrough;

connecting means connected between the first disc and the second disc within the barrel and operable to permit preselected relative movement there between so that when the second disc is moved to an operating position adjacent the barrel closed end, said one end of the cannula extends out of the barrel aperture, and when the second disc is moved to a disposal position adjacent the barrel open end, the first disc is withdrawn from the barrel closed end into a spaced-apart relationship from the second disc, in which both ends of the cannula are again disposed within the barrel;

locking means for locking the first disc in said disposal position; and manual operating means connected to said second disc and extending laterally outside of said barrel for the manual movement of said second disc from said operating position to said disposal position.

9. The blood collection device of to claim 8, and in which the locking means includes first barrel stop means disposed on the barrel between the barrel closed end and the barrel open end, second barrel stop means disposed on the barrel between the first stop means and the barrel open end, first disc stop means fixed to said first disc, and second disc stop means fixed to said second disc, and in which said first disc stop means is operable in conjunction with said first barrel stop means to prevent the passage of the first disc past the first barrel stop means in the direction of the barrel open end, the second disc stop means is operabl in conjunction with the first barrel stop means to permit the passage of the second disc past the first barrel stop means in either the direction of the barrel open end or the direction of the barrel closed end, and the second disc stop means is operable in conjunction with the second barrel stop means to permit passage of the second disc past the second barrel stop means in the direction of the barrel open end and to prevent passage of the second disc past the second barrel stop means in the direction of the barrel closed end.

10. The blood collection device of claim 9, and in which said first and second barrel stop means are each comprised by a generally L-shaped recess formed in the barrel and opening into a longitudinal passage extending substantiatily the length of the barrel, said L-shaped recesses pointing toward one another, and a first lug formed on the barrel at the opening of said recess closest to said barrel closed end and extending into the longitudinal passage so as to be undercut by its respective L-shaped recess, and a second lug formed on the barrel of the opening of said recess closest to said barrel open end and extending into the longitudinal passage so as to be undercut by its respective L-shaped recess.

11. The blood collection device of claim 10, and in which the first disc stop means is comprised by a first disc ear extending radially outwardly from said first disc into said longitudinal passage, and said second disc stop means is comprised by a second disc ear extending radially outwardly from said second disc into said longitudinal passage.

12. The blood collection device of claim 11, and in which the second disc ear has a camming surface formed thereon facing in the direction of the barrel open end and operable to deflect the first lug out of the longitudinal passage to permit the passage of the second disc thereby in the direction of the barrel open end and to deflect the second lug out of the longitudinal passage to permit passage of the second disc thereby in the direction of the barrel open end, said second ear having a stop surface formed thereon opposite said camming surface and operable when in abutment with the second lug to prevent passage of the second disc thereby in the direction of the barrel closed end, and in which said second disc ear has a digit engagable surface formed thereon to facilitate the manual movement of said disc longitudinally along said barrel.

13. The blood collection device of claim 12, and in which the first disc ear has a stop surface formed thereon facing the barrel open end and operable when in abutment with the first lug to prevent passage of the first disc thereby in the direction of the barrel open end.

14. A blood collection device of claim 13, and in which the first disc, when in the shipping position, is disposed between the first lug and the second lug, and in which the first disc ear has a camming surface formed thereon facing in the direction of the barrel closed end and operable to deflect the first lug out of the longitudinal passage to permit the passage of the first disc thereby.

15. The blood collection device of claim 13, and in which the barrel longitudinal passage has an offset opening formed so as to open thereinto adjacent the barrel closed end, said offset opening being so disposed that the second disc ear can be rotated thereinto when the second disc abuts the first disc at the barrel closed end, and locking means formed in said offset opening and operable to engage the second disc ear when rotated into said offset opening to normally retain said second disc ear in said opening.

16. The blood collection device of claim 14, and in which the barrel longitudinal passage has an offset opening formed so as to open thereinto adjacent the barrel closed end, said offset opening being so disposed that the second disc ear can be rotated thereinto when the second disc abuts the first disc at the barrel closed end, and locking means formed in said offset opening and operable to engage the second disc ear when rotated into said offset opening to normally retain said second disc ear in said opening.

17. A blood collection device as in any one of the preceding claims, and in which said connecting means are comprised by at least one flexible connecting element.

18. A blood collection device according to claim 17, and in which the flexible connecting element is substantially thread-like and inelastic.

19. A blood collection device according to claim 17, and in which the flexible connecting element is substantially thread-like and elastic.

20. In a blood collection device of the type having a barrel open at one end to permit the insertion an evacuated sample collection container therein and having an aperture at the other end to permit the extension and retraction therethrough of one end of a double-ended cannula, the combination of:
  a first disc disposed within the barrel and through which the double-ended cannula extends so as to be axially aligned within the barrel, said cannula being fixed to said first disc;
  a second disc disposed within the barrel between the first disc and the barrel open end, said second disc having an aperture axially formed therein so as to permit one end of the cannula to pass therethrough;
  a plurality of flexible string-like connectors connected between the first disc and the second disc within the barrel and operable when the second disc is moved from a first position adjacent the first disc at the barrel closed end, in which position one end of the cannula extends out of the barrel aperture, to a second position adjacent the barrel open end, to withdraw the first disc from the barrel closed end into a spaced-apart relationship from the second disc in which both ends of the cannula are disposed within the barrel;
  locking means for locking the first disc and second disc within the barrel in said spaced-apart relationship; and
  manual operating means connected to said second disc and extending laterally outside of said barrel for the manual movement of said second disc from said first position to said second position.

* * * * *